US007993362B2

(12) United States Patent
Lowe et al.

(10) Patent No.: US 7,993,362 B2
(45) Date of Patent: Aug. 9, 2011

(54) FILTER WITH POSITIONING AND RETRIEVAL DEVICES AND METHODS

(75) Inventors: Brian J. Lowe, Zimmerman, MN (US); James A. Teague, Spencer, IN (US); Mark L. Jenson, Greenfield, MN (US); Eric Welch, Miramar, FL (US); Raed N. Rizq, Fridley, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1171 days.

(21) Appl. No.: 11/058,856

(22) Filed: Feb. 16, 2005

(65) Prior Publication Data

US 2006/0184193 A1 Aug. 17, 2006

(51) Int. Cl.
*A61M 29/00* (2006.01)
(52) U.S. Cl. ...................................................... 606/200
(58) Field of Classification Search .................. 606/200, 606/113, 114, 191, 106; 623/1.11
See application file for complete search history.

(56) References Cited

U.S. PATENT DOCUMENTS

| | | |
|---|---|---|
| 4,643,184 A | 2/1987 | Mobin-Uddin |
| 4,781,177 A | 11/1988 | Lebigot |
| 4,832,055 A | 5/1989 | Palestrant |
| 4,969,891 A | 11/1990 | Gewertz |
| 5,071,407 A | 12/1991 | Termin et al. |
| 5,133,733 A | 7/1992 | Rasmussen et al. |
| 5,147,379 A | 9/1992 | Sabbaghian et al. |
| 5,221,261 A | 6/1993 | Termin et al. |
| 5,234,458 A | 8/1993 | Metais |
| 5,242,462 A | 9/1993 | El-Nounou et al. |
| 5,324,304 A | 6/1994 | Rasmussen |
| 5,407,243 A | 4/1995 | Riemann |
| 5,413,586 A | 5/1995 | Dibie et al. |
| 5,601,595 A | 2/1997 | Smith |
| 5,626,605 A | 5/1997 | Irie et al. |
| 5,669,933 A | 9/1997 | Simon et al. |
| 5,746,767 A | 5/1998 | Smith |
| 5,814,064 A | 9/1998 | Daniel et al. |
| 5,827,324 A | 10/1998 | Cassell et al. |
| 5,836,868 A | 11/1998 | Ressemann et al. |
| 5,853,420 A | 12/1998 | Chevillon et al. |
| 5,976,172 A | 11/1999 | Homsma et al. |
| 5,984,947 A | 11/1999 | Smith |
| 6,001,118 A | 12/1999 | Daniel et al. |
| 6,059,825 A | 5/2000 | Hobbs et al. |
| 6,066,158 A | 5/2000 | Engelson et al. |
| 6,126,673 A | 10/2000 | Kim et al. |
| 6,146,404 A | 11/2000 | Kim et al. |
| 6,156,055 A | 12/2000 | Ravenscroft |
| 6,171,327 B1 | 1/2001 | Daniel et al. |
| 6,179,859 B1 | 1/2001 | Bates et al. |
| 6,187,025 B1 | 2/2001 | Machek |

(Continued)

OTHER PUBLICATIONS

US 2004/0199198 A1, published Oct. 7, 2004, Baulke et al.

(Continued)

*Primary Examiner* — Anhtuan T Nguyen
*Assistant Examiner* — Amy Lang
(74) *Attorney, Agent, or Firm* — Seager, Tufte & Wickhem LLC

(57) ABSTRACT

An intravascular filter having centering capabilities and a device for manipulation of the filter within a vessel. The manipulation device includes a grasping member disposed at the distal end of an elongate shaft, wherein the grasping member may be used to engage a portion of the filter.

22 Claims, 16 Drawing Sheets

U.S. PATENT DOCUMENTS

| | | |
|---|---|---|
| 6,214,025 B1 | 4/2001 | Thistle et al. |
| 6,214,026 B1 | 4/2001 | Lepak et al. |
| 6,231,589 B1 | 5/2001 | Wessman et al. |
| 6,258,026 B1 | 7/2001 | Ravenscroft et al. |
| 6,325,815 B1 | 12/2001 | Kusleika et al. |
| 6,336,934 B1 | 1/2002 | Gilson et al. |
| 6,338,735 B1 | 1/2002 | Stevens |
| 6,342,062 B1 * | 1/2002 | Suon et al. .................. 606/200 |
| 6,346,116 B1 | 2/2002 | Brooks et al. |
| 6,364,895 B1 | 4/2002 | Greenhalgh |
| 6,375,670 B1 | 4/2002 | Greenhalgh |
| 6,383,205 B1 | 5/2002 | Samson et al. |
| 6,391,044 B1 | 5/2002 | Yadav et al. |
| 6,432,122 B1 | 8/2002 | Gilson et al. |
| 6,443,972 B1 | 9/2002 | Bosma et al. |
| 6,468,290 B1 | 10/2002 | Weldon et al. |
| 6,540,722 B1 | 4/2003 | Boyle et al. |
| 6,540,768 B1 | 4/2003 | Diaz et al. |
| 6,544,279 B1 | 4/2003 | Hopkins et al. |
| 6,558,405 B1 | 5/2003 | McInnes |
| 6,569,183 B1 | 5/2003 | Kim et al. |
| 6,569,184 B2 | 5/2003 | Huter |
| 6,589,263 B1 | 7/2003 | Hopkins et al. |
| 6,596,011 B2 | 7/2003 | Johnson et al. |
| 6,602,271 B2 | 8/2003 | Adams et al. |
| 6,616,680 B1 | 9/2003 | Thielen |
| 6,623,506 B2 | 9/2003 | McGuckin, Jr. et al. |
| 6,645,224 B2 | 11/2003 | Gilson et al. |
| 6,692,458 B2 * | 2/2004 | Forman et al. ............. 604/93.01 |
| 2001/0023358 A1 * | 9/2001 | Tsukernik .................... 606/200 |
| 2003/0181945 A1 | 9/2003 | Opolski et al. |
| 2004/0225322 A1 | 11/2004 | Garrison et al. |
| 2005/0055046 A1 * | 3/2005 | McGuckin et al. ........... 606/200 |
| 2005/0159771 A1 * | 7/2005 | Petersen ....................... 606/200 |
| 2007/0055303 A1 * | 3/2007 | Vidlund et al. ............... 606/213 |

OTHER PUBLICATIONS

US 2003/0097145 A1, published May 22, 2003, Goldberg et al.
US 2002/0116024 A1, published Aug. 22, 2002, Goldberg et al.

* cited by examiner

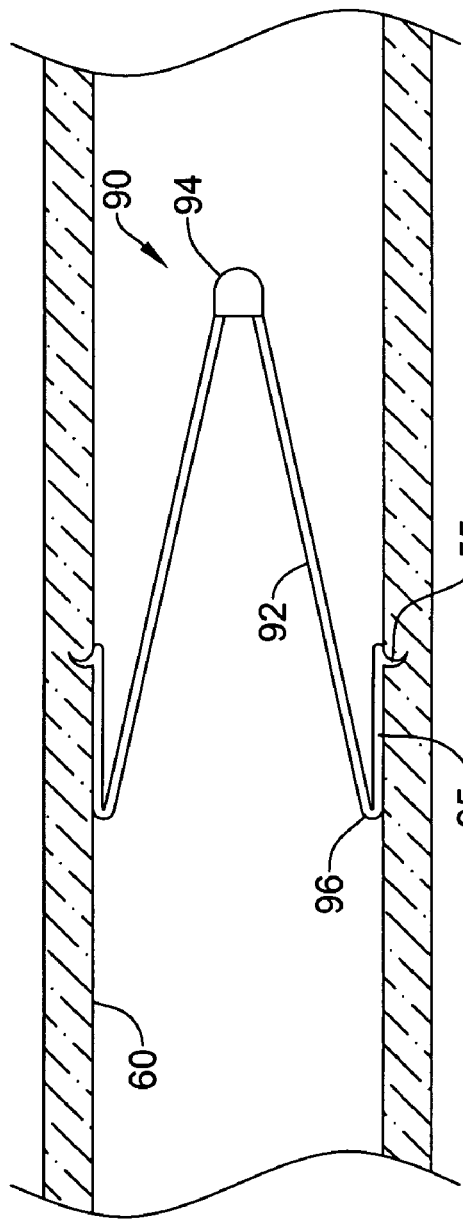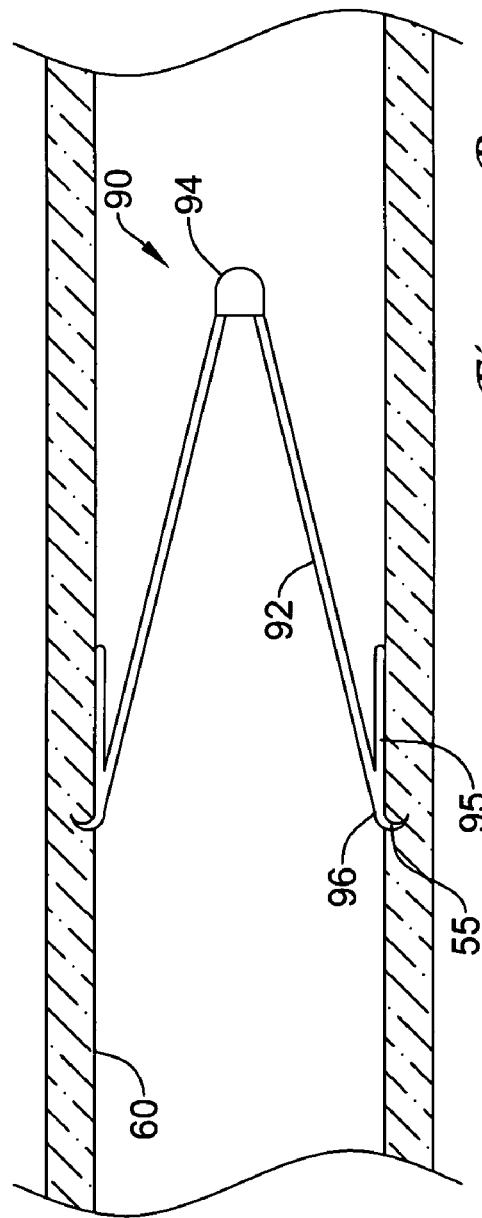

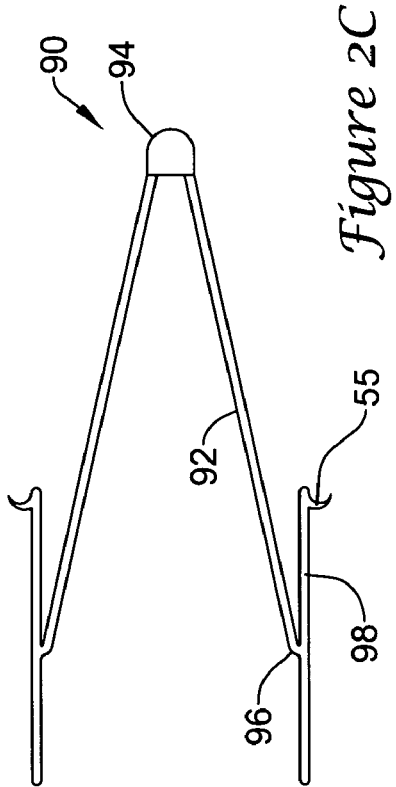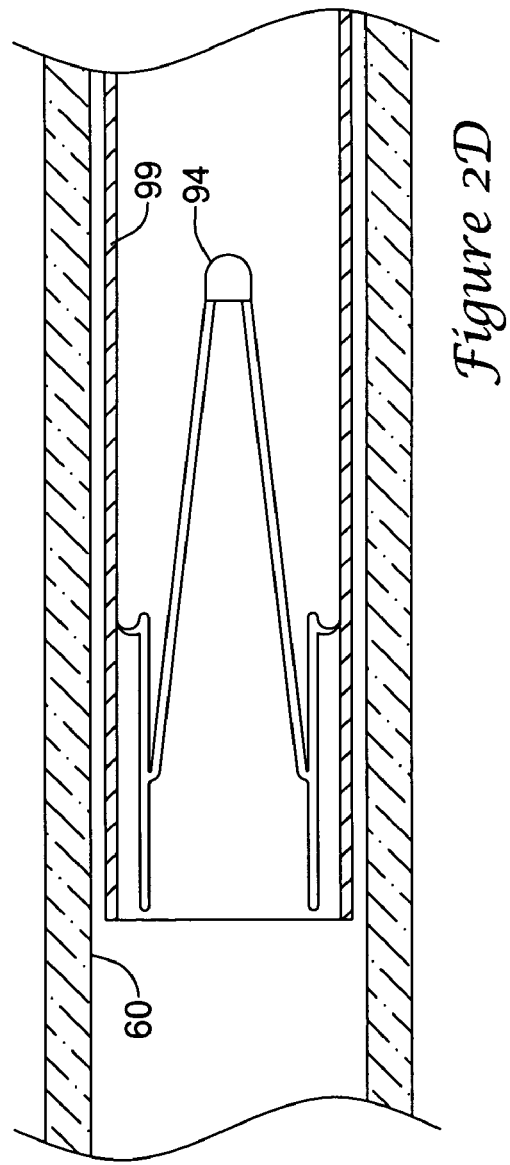

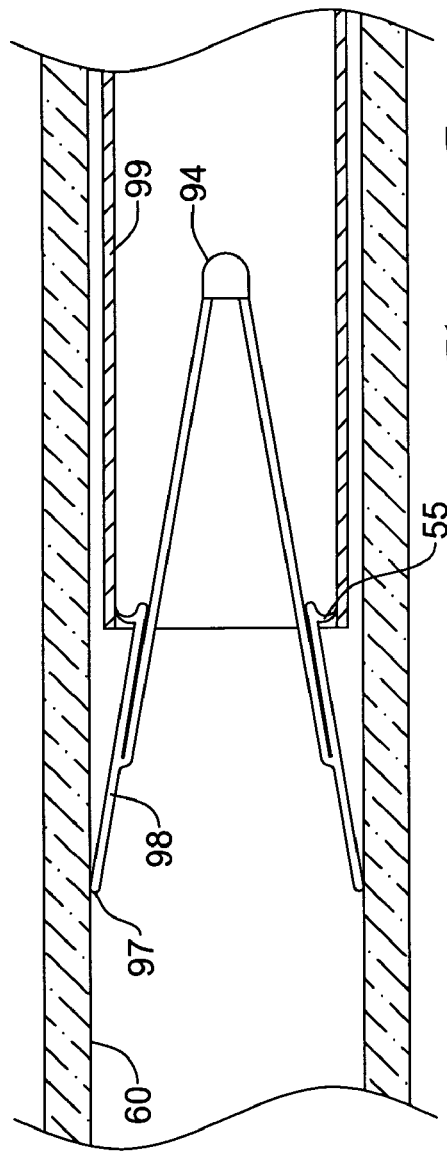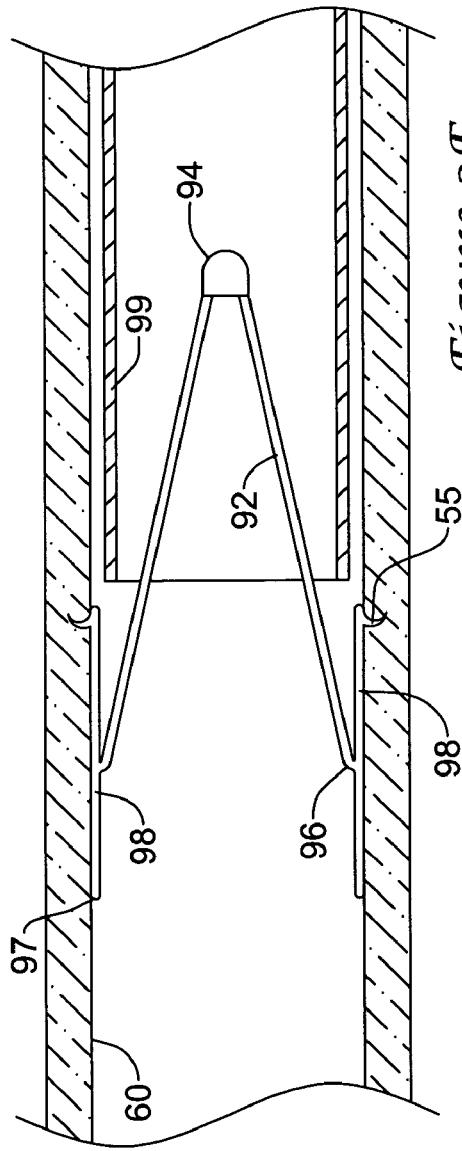

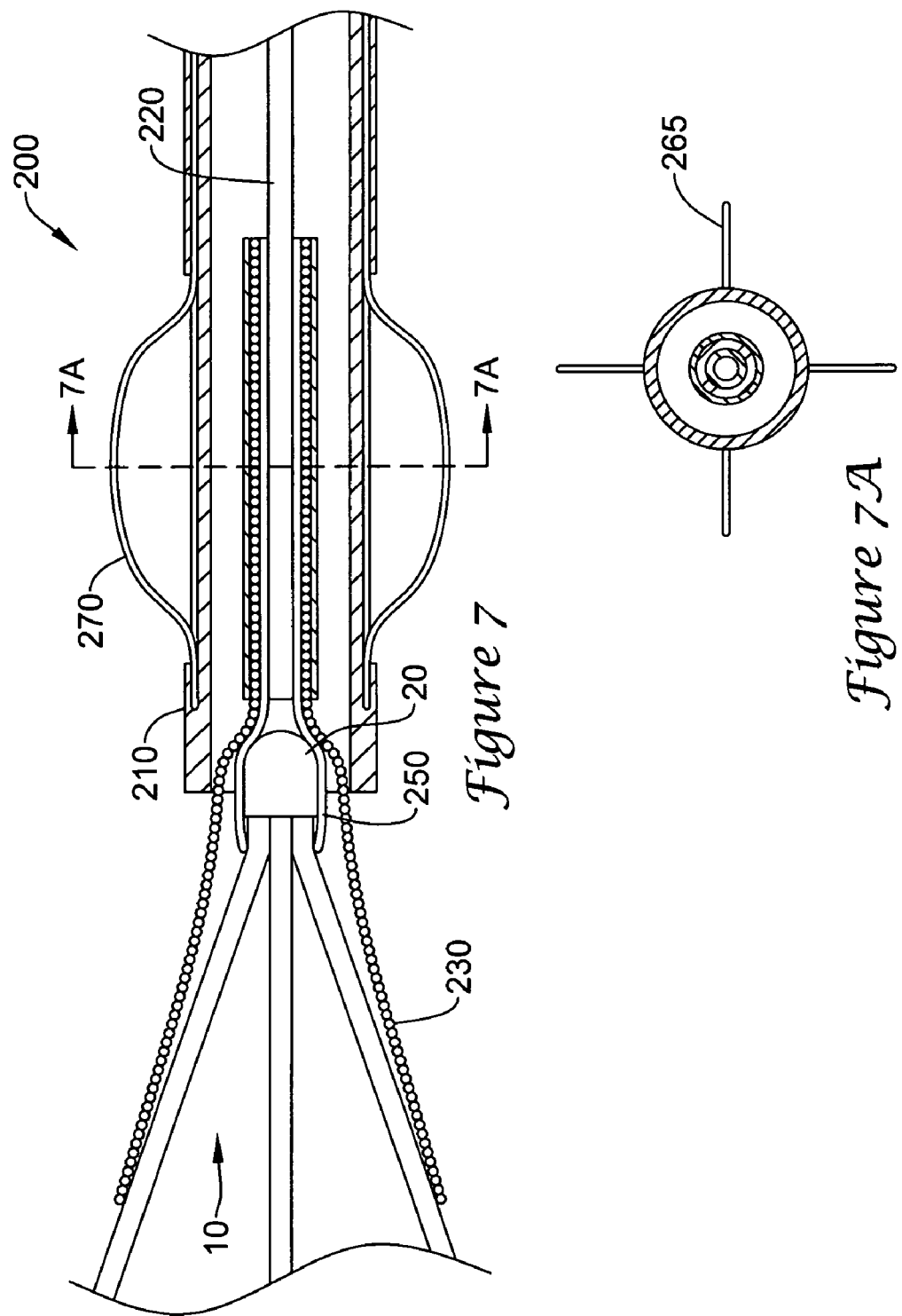

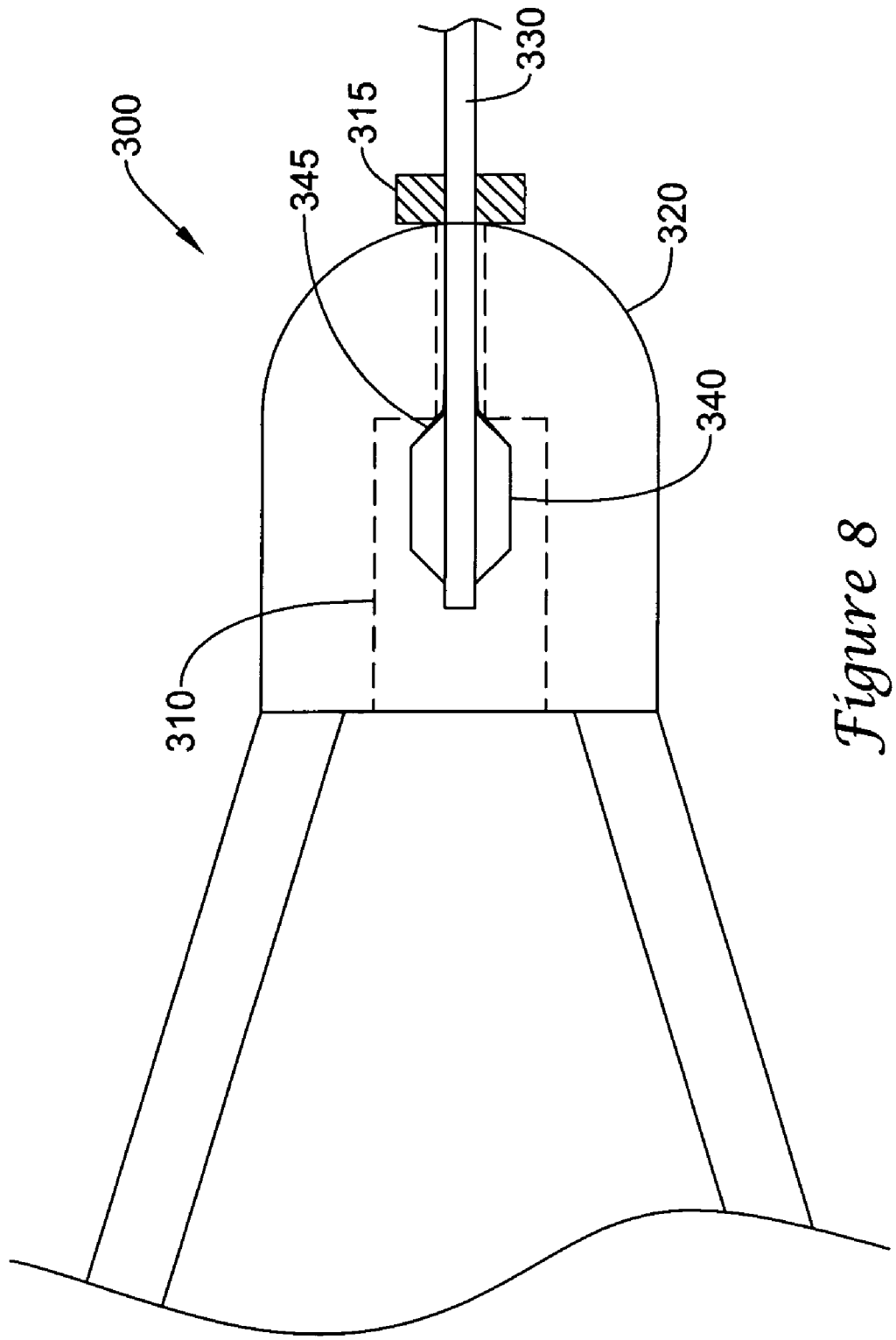

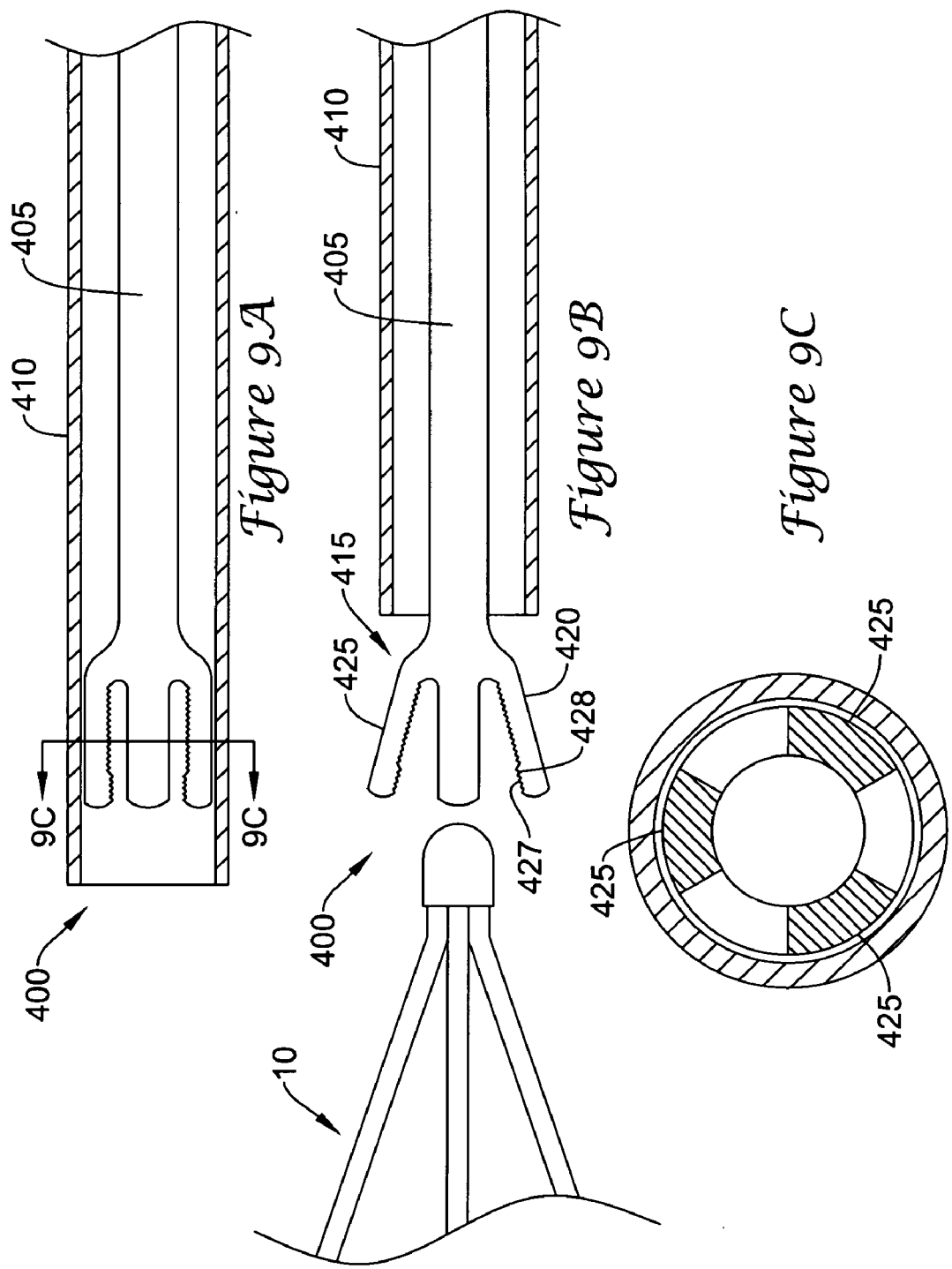

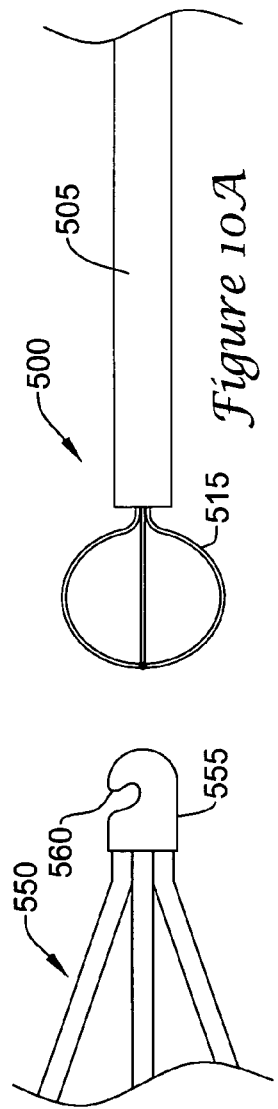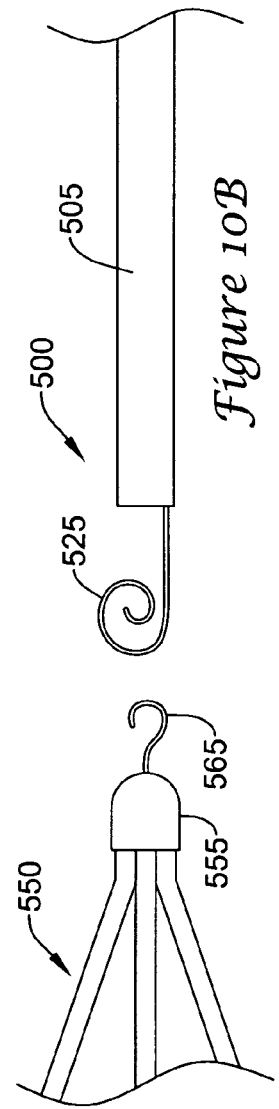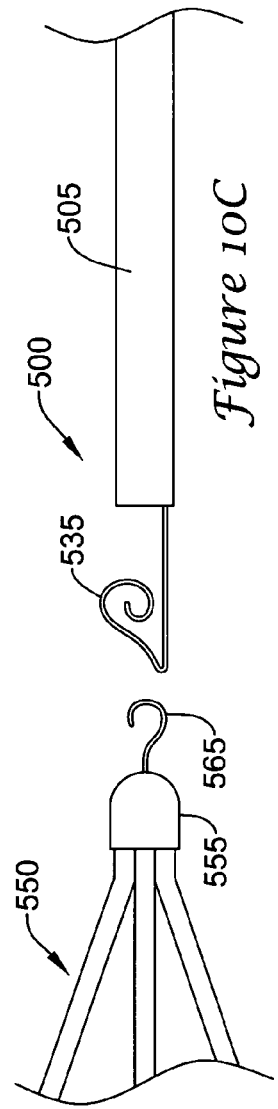

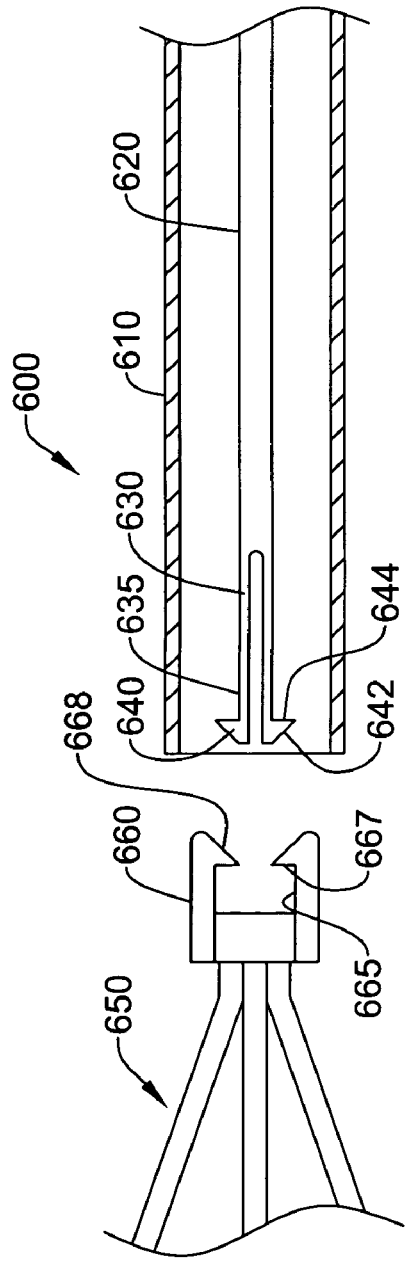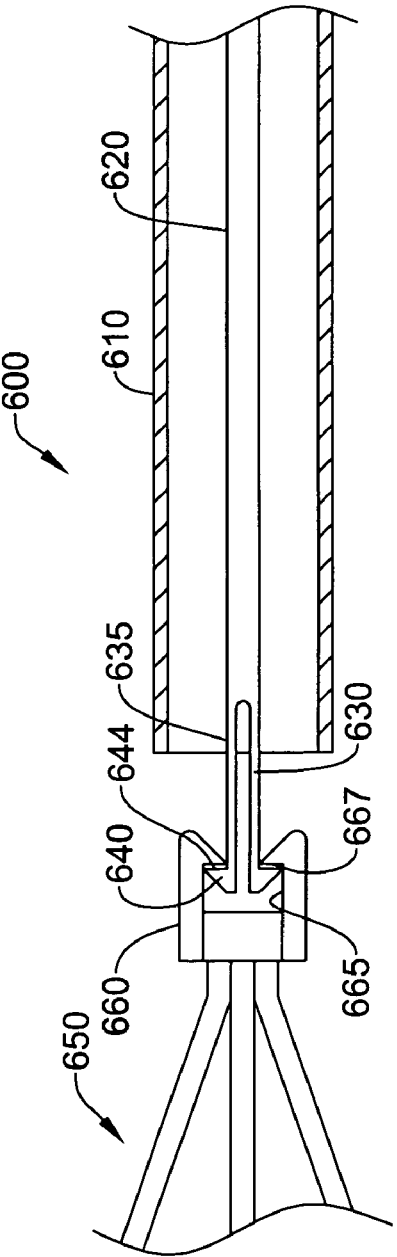
Figure 11A
Figure 11B

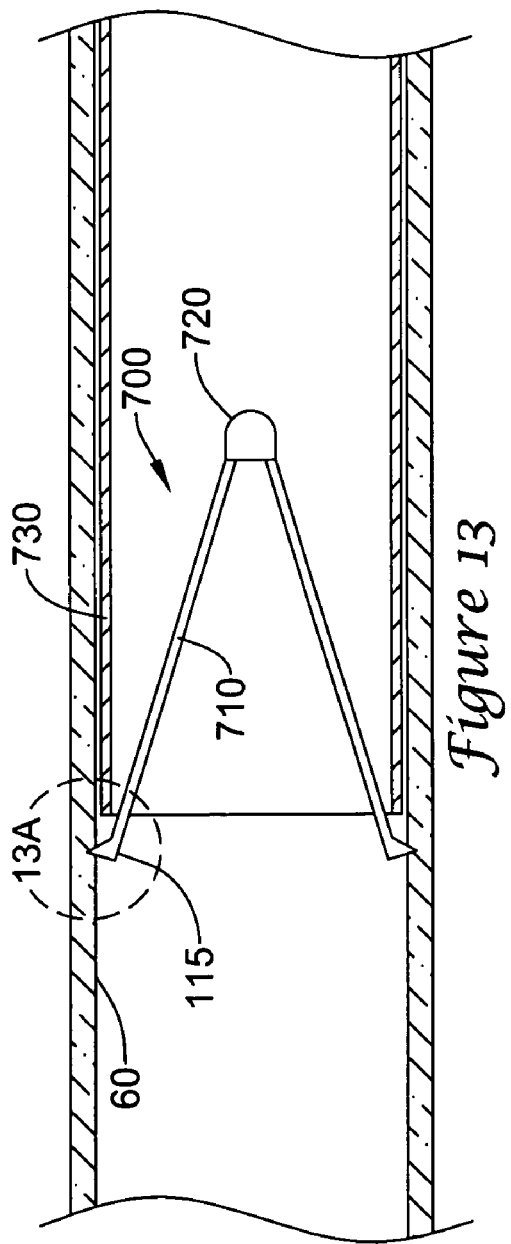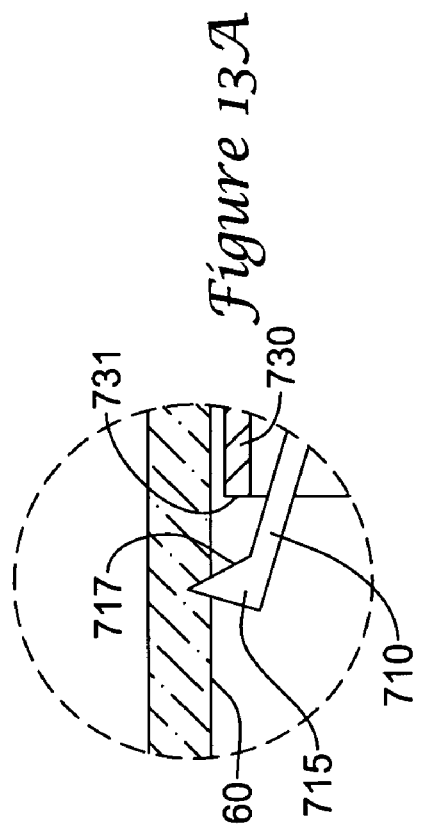

FILTER WITH POSITIONING AND RETRIEVAL DEVICES AND METHODS

FIELD OF THE INVENTION

The invention generally relates to filter devices for trapping blood clots and controlling embolization and thrombosis in blood vessels. More specifically, the present invention is directed to an improved filter and methods and devices for positioning and retrieving the same.

BACKGROUND OF THE INVENTION

Intravenous filters are commonly used to trap blood clots (emboli) carried in the vasculature. Such emboli may cause serious health risks including embolization and thrombosis, and may ultimately lead to death. Such emboli, if left unrestrained, may travel to the lungs through the vasculature, resulting in pulmonary embolism. A filtering device may be positioned in a blood vessel, such as the vena cava, in order to capture emboli and prevent emboli from reaching the lungs.

It is difficult to precisely and accurately deploy a filter in a blood vessel. The filter can be deployed in a tilted position, i.e., not centered within the vessel. Filters positioned in such an orientation may not function as well as well-centered filters. There is a continuing need to more accurately control the deployment of an intravenous filter within a blood vessel, such that the filter is centered in the vessel.

Additionally, it may be necessary to remove a filter from the vessel once the health threat has been removed. There is a continuing need to provide an easily retrievable filter and/or retrieval device that can remove a filter without subjecting the walls of the vessel to unnecessary trauma. Current filters may damage the vessel wall during a removal process.

SUMMARY OF THE INVENTION

The invention pertains to an intravenous filter that can be more accurately centered within a vessel. The invention is also directed to a deployment and/or retrieval device for positioning a filter in a vessel.

Accordingly, one embodiment includes an expandable filter having multiple sets of centering legs. The orientation of the centering legs provides an elongated cylindrical area for more accurately centering the filter within a vessel. Alternatively, the filter may have elongated feet attached to the filter legs to more accurately center and stabilize the filter within a vessel.

Another embodiment includes a placement device for deploying, repositioning, or withdrawing a filter within a vessel. The placement device includes an inner elongate member and an outer sheath disposed about the inner elongate member. The inner elongate member is connected to a grasping member extending distal of the inner elongate member. The grasping member may be biased in an expanded configuration, but may be collapsed to engage a filter when the outer sheath is extending distally. Such a device may be used to deploy a filter within a vessel, reposition a filter within a vessel, or it may be used to extract a filter from a vessel. As used herein, manipulating a filter in a vessel includes deploying, repositioning, extracting, or the like.

Additional embodiments are contemplated as discussed in the detailed description of preferred embodiments. The enclosed embodiments are only illustrative, and are not intended to be exhaustive embodiments of the invention.

BRIEF DESCRIPTION OF THE DRAWINGS

The invention may be more completely understood in consideration of the following detail description of various embodiments of the invention in connection with the accompanying drawings, in which:

FIGS. 2A and 2B are plan views of exemplary intravascular filters within the scope of the invention.

FIGS. 2C-2F are plan views of a filter in accordance with the invention and means for deploying a filter within a vessel.

FIG. 7 is a cross-sectional view of a filter manipulation device in accordance with the invention.

FIG. 7A is a cross-sectional view of the filter manipulation device in FIG. 7 taken along line 7A-7A.

FIG. 8 is a cross-sectional view of a filter and filter retrieval device within the scope of the invention.

FIGS. 9A-9C are cross-sectional views of a filter retrieval device within the scope of the invention.

FIGS. 10A-10C are plan views of illustrative embodiments of a filter retrieval device within the scope of the invention.

FIGS. 11A-11B are cross-sectional views of a filter and filter retrieval device in accordance with the invention.

FIGS. 13-13A are cross-sectional views of a method for retrieving a filter in accordance with the invention.

DETAILED DESCRIPTION OF PREFERRED EMBODIMENTS

The following detailed description should be read with reference to the drawings in which similar elements in different drawings are numbered the same. The detailed description and the drawings, which are not necessarily to scale, depict illustrative embodiments and are not intended to limit the scope of the invention.

Figure 1:
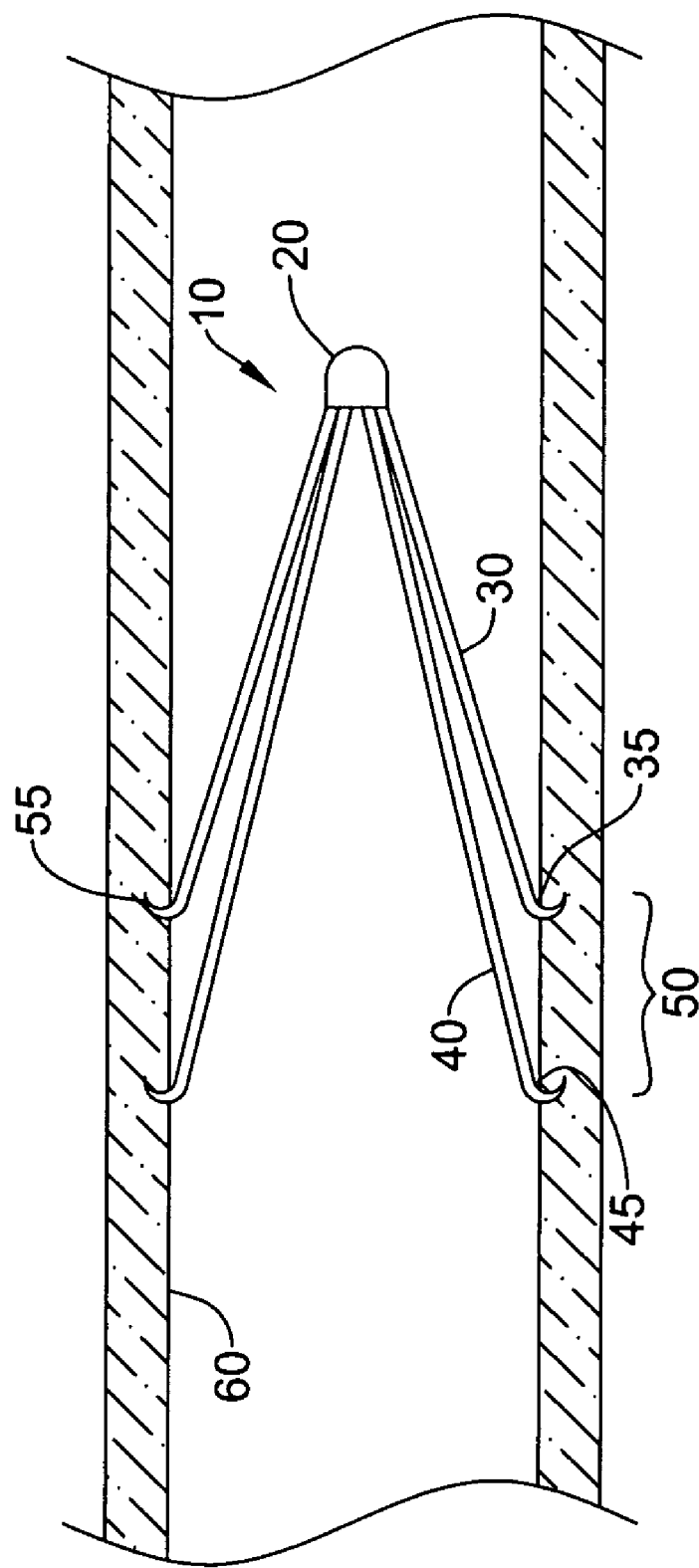
FIG. 1 is a plan view of an intravascular filter within the scope of the invention.

FIG. 1 shows one embodiment of an intravenous filter according to the invention. Filter 10 includes a tip 20 and multiple sets of legs 30, 40 extending from tip 20. FIG. 1 depicts a filter having two sets of legs, but a filter having additional sets of legs is contemplated as being within the scope of the invention. Legs 40 are longer than legs 30, thereby creating a landing distance 50 between distal end 35 of legs 30 and distal end 45 of legs 40. The landing distance 50 may resemble a cylindrical wall between distal ends 35, 45 of legs 30, 40. The landing distance 50 provides an elongated planar surface for the filter 10 to engage the wall 60 of a vessel. By engaging the wall 60 at multiple distances from the filter tip 20, the filter 10 may be more accurately centered in a vessel.

One set of legs may include securing hooks 55 at the distal end 35, 45 of legs 30, 40. Securing hooks 55 prevent the filter 10 from migrating downstream or tilting after deployment. Hooks 55 may comprise thermally reactive metals, such as shape memory alloys. Preferably, hooks may comprise a nickel-titanium alloy such as nitinol. Hooks 55 comprising a thermally reactive metal may be subjected to thermal energy, such as an electrical charge, non-invasive RF energy, or the like. Hooks 55 subjected to thermal energy may tend to straighten to facilitate disengagement from the vessel wall 60 during a filter retrieval process. As hooks 55 straighten as a result of subjecting them to a thermal energy source, hooks 55 lose their anchoring ability, therefore, allowing the filter 10 to be disengaged from the vessel.

FIG. 2A shows another embodiment of the invention. Filter 90 includes a plurality of legs 92 extending from the tip 94. A longitudinal landing foot 95 is connected to each leg 92 at distal end 96. Landing feet 95 provide an elongated planar surface for the filter 90 to engage the wall 60 of a vessel. The elongated planar surface formed by the landing feet 95 may more accurately center the filter 90 in a vessel. A securing hook 55 may be disposed at the proximal end of each landing foot 95 in order to engage the vessel wall 60. Alternatively, securing hooks 55 may be disposed at the distal end of each landing foot 95 as shown in FIG. 2B. The location of securing hooks 55 may be determined by the method of deployment or retrieval of the filter 90 from a vessel.

FIG. 2C shows an alternate embodiment of the filter 90 of FIGS. 2A, 2B. Filter 90 has centering feet 98 attached at distal ends 96 of legs 92. Centering feet 98 extend both proximally and distally from distal end 96 of legs 92. Centering feet 98 may provide a longer longitudinal distance for centering the filter 90 than feet 95. Centering feet 98 provide greater control for anchoring and centering the filter 90 within a vessel. Greater control is accomplished because centering feet 98 exit deployment sheath first, allowing for a gradual expansion of filter 90, as opposed to a sudden "jump" in expansion as is common with prior art filters. As shown in FIG. 2D, prior to deployment centering feet 98 are substantially longitudinal with deployment sheath 99. As deployment sheath 99 is retracted proximally, feet 99 are moved distal of deployment sheath 99 and begin to tilt radially outward. As shown in FIG. 2E, distal ends 97 of centering feet 98 engage vessel wall 60 initially. Because a portion of centering feet 98 remain contained within deployment sheath 99, the filter 90 does not rapidly expand, prior to engagement of centering feet 98 with the vessel wall 60. Deployment sheath 99 may then be further retracted proximally to release filter 90 within the vessel as shown in FIG. 2F. Centering feet 98, thereafter, facilitate centering of filter 90 within the vessel as the filter 90 expands.

Figure 3A:
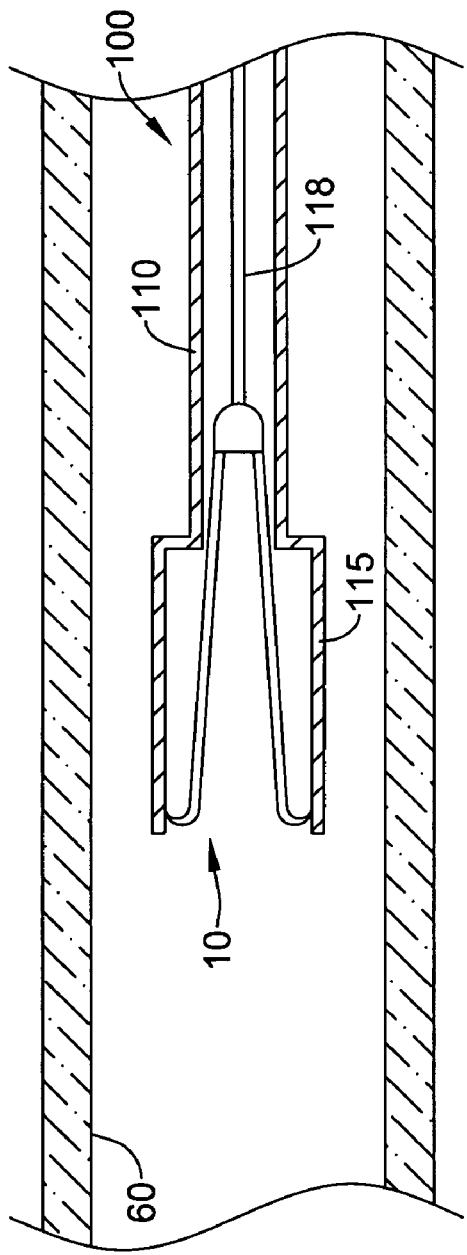
FIGS. 3A-3B are partial cross-sectional views of a filter deployment device and method within the scope of the invention.
Figure 3B:
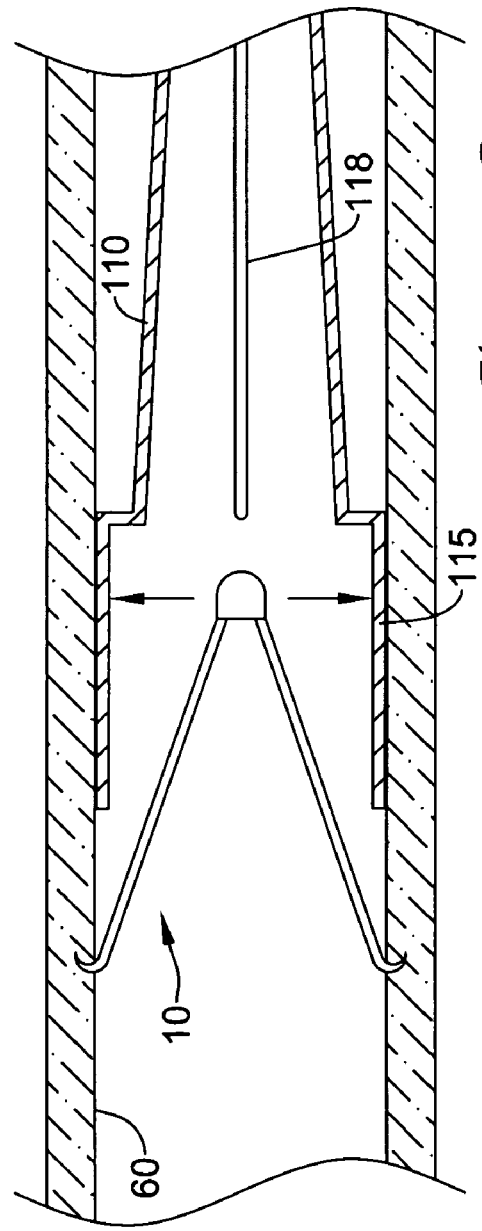

FIG. 3A shows a delivery device 100 for delivering a filter such as filter 10. Delivery device 100 includes an elongated shaft 110. Elongated shaft 110 has a distal segment 115 having an enlarged diameter relative to the portion of elongated shaft 110 proximate the distal segment 115. Distal segment 115 may include a shape memory polymer (SMP), such that when the SMP is subjected to a thermal energy source increasing its temperature above its glass transition temperature (Tg), the distal segment 115 may transform to a preformed shape. Such a preformed shape may have an expanded diameter. Filter 10 may be disposed within distal segment 115 prior to deployment. Push wire 118 may extend through elongated shaft 110 to filter 10. Push wire may abut filter 10 or may be releasably attached to filter 10. As shown in FIG. 3B, the enlarged distal segment 115 may be subjected to a thermal energy source, allowing the distal segment 115 to be expanded to abut the wall 60 of a vessel prior to deployment of the filter 10. The expanded state of enlarged distal segment 115 allows the filter 10 to be partially expanded within the distal segment 115 prior to deployment within the vessel. Partially expanding the filter 10 in the distal segment 115 prior to deployment minimizes the additional amount ("jump") the filter 10 must expand after deploying the filter distal of the distal segment 115. By minimizing the jump the filter must undergo in order to engage the vessel wall 60, the filter 10 may be more precisely centered in the vessel.

Figure 4:
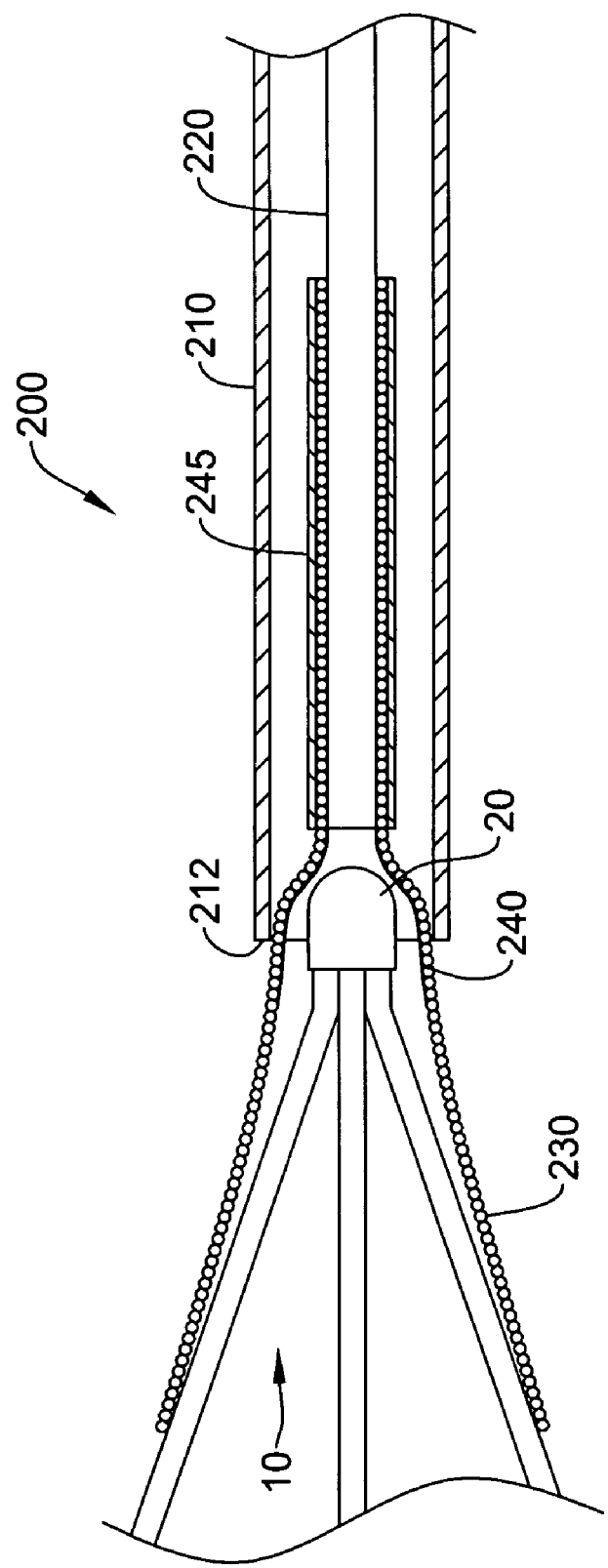
FIG. 4 is a cross-sectional view of a filter manipulation device in accordance with the invention.

FIG. 4 shows a filter manipulation device 200 in accordance with the invention. Filter manipulation device 200 may be used as a delivery device, a repositioning device, or a retrieval device. Filter manipulation device 200 includes an outer sheath 210 and a push/pull wire 220 disposed within outer sheath 210. A first braided member 230 may be disposed about a portion of distal end of push/pull wire 220 and extend distally therefrom. Alternatively, first braided member 230 may be disposed adjacent to clip 240 and extend distally therefrom. The first braided member 230 may comprise a polymer, a metal, such as a stainless steel alloy, or the like. Some suitable materials may include stainless steels (e.g., 304v stainless steel), nickel-titanium alloys (e.g., nitinol, such as super elastic or linear elastic nitinol), nickel-chromium alloys, nickel-chromium-iron alloys (e.g., Inconel®), cobalt alloys, nickel, titanium, platinum, or alternatively, a polymer material such as a high performance polymer, or other suitable materials, and the like. Preferably, first braided member 230 may include a nickel-titanium alloy. The first braided member 230 may be braided in a one-over-one configuration, a two-over-one configuration, or the like.

First braided member 230 may substantially comprise a conical shape. A proximal portion of first braided member 230 may extend over distal end of push/pull wire 220, or may be secured to distal end of push/pull wire 220. First braided member 230 may be secured to the distal portion of push/pull wire 220 with a tubular sleeve. Tubular sleeve, may be heat shrink tubing, a polymer jacket, a metallic band, or the like. Preferably, first braided member 230 may be secured to push/pull wire 220 with a hypotube 245. Hypotube 245 may be an elongated metallic tube including a stainless steel or nickel-titanium alloy. Hypotube 245 may include a helical cut or a plurality of apertures formed in at least a portion of the hypotube 245.

First braided member 230 may be formed to be biased in an expanded configuration as shown in FIG. 4, but may be contracted within outer sheath 210 by moving outer sheath 210 in the distal direction during a delivery or removal process. The first braided member 230 may abut filter 10 in an expanded configuration. The first braided member 230 may act as a wedge to capture the filter 10. Frictional forces between the first braided member 230 and the filter 10 hold the filter 10 adjacent the first braided member 230 and provide purchase during manipulation of the filter 10. Moving outer sheath 210 in the distal direction allows the distal end 212 of outer sheath 210 to contact the first braided member 230, such that braided member 230 is compressed at least partially within outer sheath 210. Braided member 230 provides sufficient purchase of the filter 10 due to the frictional contact between the interface of the first braided member 230 and filter 10. The purchase created by the frictional contact is sufficient to allow the manipulation device 200 to maneuver and position the filter 10. As outer sheath 210 is moved in the distal direction, first braided member 230 collapses filter 10 to a collapsed state sufficient to retain filter 10 within outer sheath 210.

The distal end of push/pull wire 220 may include a clip 240, preferably comprising a nickel-titanium alloy, such as nitinol. Clip 240 may be formed such as by heat setting with a curved shape so as to open as the outer sheath 210 is retracted proximally. Clip 240 may be a substantially conical shaped. Clip 240 may be formed to extend over and grasp the tip 20 of a filter 10. Clip 240 may be secured to push/pull wire 220 by a sleeve, heat shrink member, adhesive, welding, or any other ways known in the art. Preferably, clip 240 is secured to push/pull wire 220 with a tubular member comprising a polymer or metallic alloy. Preferably clip 240 is secured to push/pull wire 220 with hypotube 245. Clip 240 may contact the tip 20 of filter 10 as outer sheath 210 is extended distally. Clip 240 may collapse and securely encompass tip 20 once outer sheath 210 is extended distally. Frictional contact with filter 10 created by clip 240 and/or first braided member 230 may allow manipulation of filter 10 within a vessel.

Outer sheath 210 may be partially retracted proximally, allowing first braided member 230 to expand partially. Partially expanded first braided member 230 is thus disengaged from the filter 10, while clip 240 remains secured about tip 20 of filter 10 due to the continued engagement of outer sheath 210 about clip 240. Thus, the operator may continue to control the position of the filter 10 prior to retracting outer sheath 210 fully. Once filter 10 has been positioned in a vessel, outer sheath 210 may then be retracted fully, disengaging manipulation device 200 from filter 10.

Figure 5:
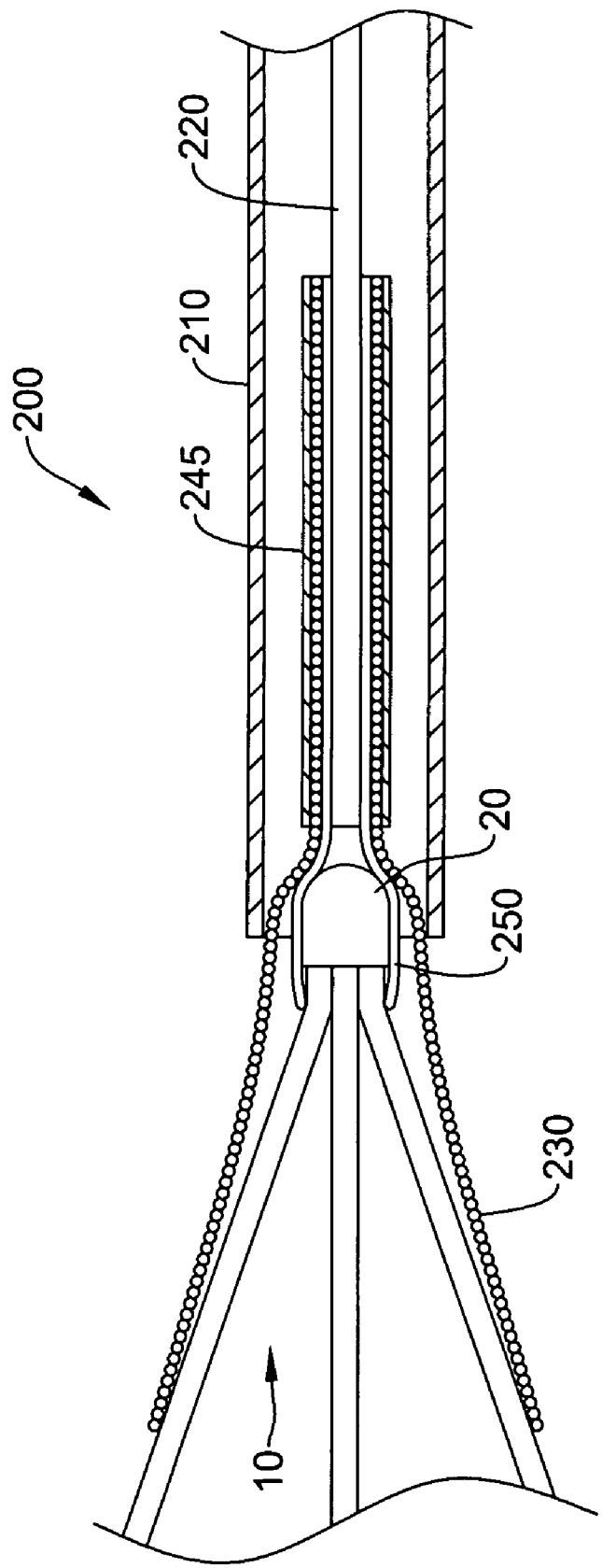
FIG. 5 is a cross-sectional view of a filter manipulation device in accordance with the invention.

FIG. 5 shows an alternate embodiment of manipulation device 200. Manipulation device 200 may optionally include second braided member 250 disposed about push/pull wire 220 and extending distally therefrom. Second braided member 250 may be included instead of or in addition to clip 240. Similar to clip 240, second braided member 250 may engage filter tip 20 as outer sheath 210 is extended distally. Frictional forces between second braided member 250 and filter tip 20 may hold filter 10 adjacent to manipulation device 200. Second braided member 250 may extend substantially the length of hypotube 245, or second braided member 250 may extend a portion thereof. First braided member 230 may be disposed adjacent to second braided member 250 and may also extend substantially the length of hypotube 245, or a portion thereof.

Figure 6:
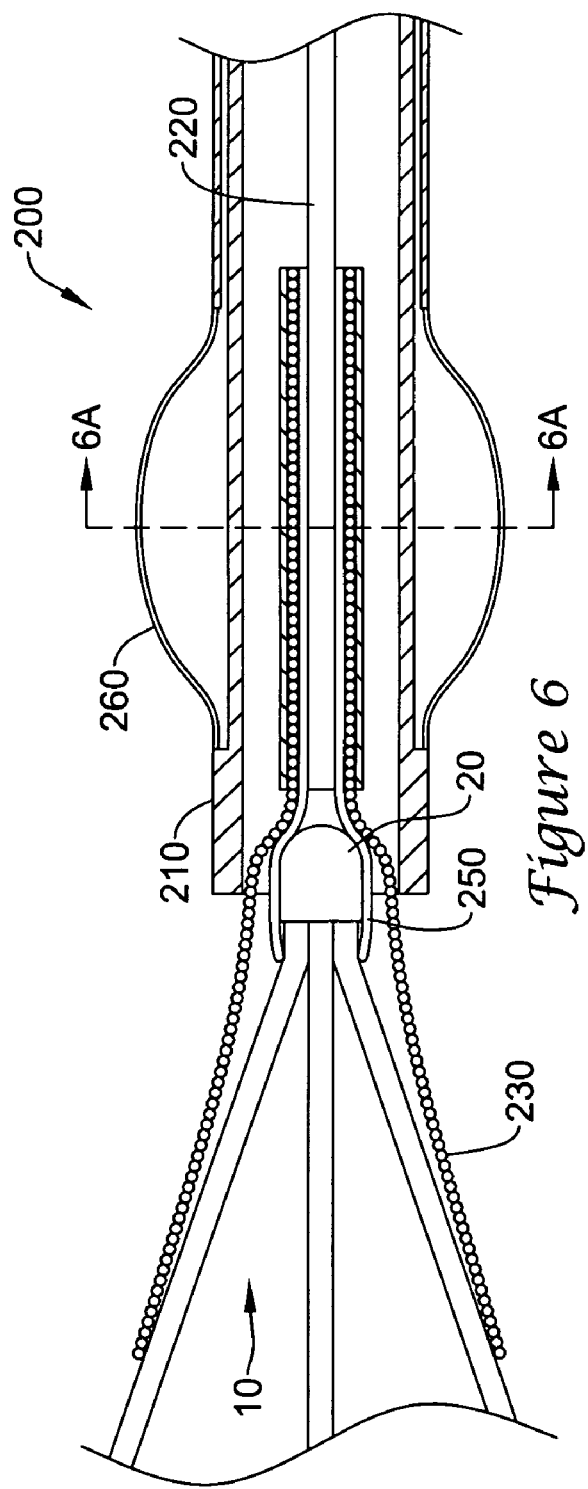
FIG. 6 is cross-sectional view of a filter manipulation device in accordance with the invention.
Figure 6A:
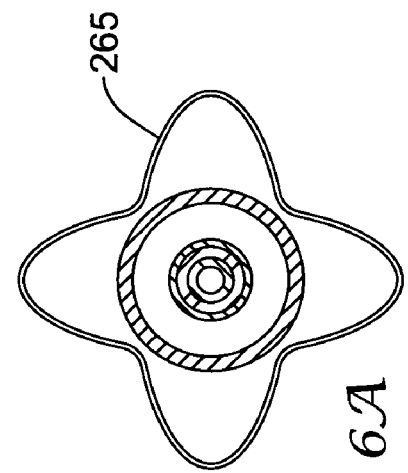
FIG. 6A is a cross-sectional view of the filter manipulation device in FIG. 6 taken along line 6A-6A.

As shown in FIG. 6, manipulation device 200 may include an inflatable balloon 260 disposed about a distal portion of outer sheath 210. Inflatable balloon 260 may be a single balloon disposed concentrically about outer sheath 210 or may comprise a plurality of lobes 265. As shown in FIG. 6A, balloon 260 may comprise four inflatable lobes 265 spaced equidistantly about outer sheath 210, i.e., at 90 degree intervals. Inflatable balloon 260 may be inflated through catheter inflation port (not shown) to center the manipulation device 200 within a body vessel. Centering the manipulation device 200 within a body vessel may facilitate centering the filter 10 during a delivery process or capturing the filter 10 during a retrieval process. The use of balloon 260 having a plurality of lobes 265 allows for continued blood flow through the vessel while the balloon 260 is inflated.

Alternatively, as shown in FIG. 7, manipulation device 200 may include a plurality of wires 270. As shown in FIG. 7A, manipulation device 200 may include a plurality of wires 270 spaced about outer sheath 210. Preferably, manipulation device 200 includes four wires 270 spaced equidistantly about outer sheath 210, i.e., at 90 degree intervals. Wires 270 may have a circular cross-section or may be substantially flat. Wires 270 may comprise a polymer, a metal, or the like. Preferably, wires 270 comprise a nickel-titanium alloy, such as nitinol. Wires 270 preferably are heat set in a curved shape such that wires 270 abut the vessel wall 60 when in an open position. An actuation rod (not shown) extending through the catheter may be used to direct the wires 270 between an open and a closed position. Alternatively, wires 270 may be actuated to an opened position by exposing wires to a thermal energy source, such as an electrical charge, RF heating, or the like. Wires 270, similar to balloon 260, may facilitate centering the manipulation device 200 within the vessel wall 60 during a filter manipulation process. Wires 270 allow for continued blood flow through the vessel while the wires 270 are in an open position.

FIG. 8 shows an alternate embodiment of a filter retrieval device in accordance with the invention. Filter 300 includes a tip 320 having a lumen 310 extending therethrough. As shown in FIG. 8, lumen 310 may include a step-wise transition in diameter within the tip 320. An elongate shaft 330 having an expandable member 340 disposed at the distal end thereof may be extended through the lumen 310. A stop 315 may be disposed about elongate shaft 330 at a predetermined distance from expandable member 340. Stop 315 may be positioned such that stop 315 abuts the tip 320 just as expandable member 340 extends past the step-wise transition of lumen 310. Therefore, an operator may know the expandable member 340 is correctly positioned relative to the filter 300 during a retrieval process when the operator feels the stop 315 abut the tip 320 of filter 300.

As shown in FIG. 8, the expandable member 340 may be an inflatable balloon. Expandable member 340 may include a protective material 345 at the proximal end of expandable member 340. The protective material 345 may create a barrier between the expandable member 340 and the filter tip 320, thus protective material 345 may enhance the durability of expandable member 340. The protective material 345 may be conical shaped, pedal shaped, or the like, and may comprise a metal or polymer.

After the elongate shaft 330 and expandable member 340 are extended through the lumen 310, the expandable member may be expanded. Once in an expanded state, the elongate shaft may be pulled proximally, thereby shifting the filter in the proximal direction during a filter retrieval process.

An alternate embodiment of a retrieval device within the scope of the current invention is shown in FIGS. 9A, 9B and 9C. Retrieval device 400 may include an elongate shaft 405 and an outer sheath 410. Elongate shaft 405 may be disposed in outer sheath 410. Distal portion 415 of elongate shaft 405 may include grasping tongs 420, such as forceps or pincers. Preferably, tongs 420 may be an integral portion of elongate shaft 405. Preferably, tongs 420 may be laser cut in the distal portion 415 of elongate shaft 405. Tongs 420 may include a plurality of appendages 425. As shown more clearly in FIG. 9C, tongs 420 may include three equidistantly spaced appendages 425. Tongs 420 may comprise a polymer, a metal, or the like. Appendages 425 preferably are biased in an open position as shown in FIG. 9B. Appendages 425 may be biased in an open position during a heat set process, such as steam setting. Appendages 425 may have an abrasive surface such as ridges 427 and grooves 428 to facilitate griping a filter such as filter 10.

During a filter retrieval process, tongs 420 are collapsed in outer sheath 410 and delivered near the filter 10. Outer sheath 410 is then retracted proximally, thereby allowing tongs 420 to extend distal of the outer sheath 410. Once appendages 425 are exposed from outer sheath 410, appendages 425 expand to their biased open position. Tongs 420 are then moved over filter 10. Outer sheath 410 is then extended distally over tongs 420 forcing tongs 420 to collapse around filter 10. Preferably, tongs 420 collapse around tip 20. Outer sheath 410 prevents tongs 420 from expanding, therefore retaining the filter 10. The elongate shaft 400 and outer sheath 410 may then be retracted from the vessel, wherein tongs 420 retain filter 10.

FIGS. 10A-10C illustrate another retrieval device 500 in accordance with the invention. Instead of tongs, retrieval device 500 may include an elongate shaft 505 having a grasping member such as loop 515, shepherd's hook 525 or atraumatic hook 535 for grasping a filter. A filter such as filter 550 may include a tip 555 having mating geometry adapted to receive the grasping member of retrieval device 500. Such mating geometry may include a hook 560, 565. Elongate shaft 505 may be extended through a vessel to filter 550. Grasping member, such as loop 515, is positioned to mate with and grasp filter 550 by hook 560, 565. Elongate shaft 505 may then be retracted, withdrawing filter 550 from the vessel. Grasping members such as shown in FIGS. 10A-10C provide an operator with a greater margin of error in directing a retrieval device to a filter.

Another illustrative retrieval device is shown in FIGS. 11A-11B. Retrieval device 600 may include an outer sheath 610 and an elongate shaft 620. Elongate shaft 620 may include a clasp 630 disposed at the distal end of elongate shaft 620. Preferably, clasp 630 may be formed as an integral portion of elongate shaft 620. Clasp may include a plurality of appendages 635 laser cut about the circumference of elongate shaft 620. Appendages 635 include locking geometry such as barbs 640. Barbs 640 include a ramp 642 and a shelf 644. Filter 650 may include a tip 660 having complimentary interlocking geometry. Tip 660 may include a lumen 665 having a beveled surface 668. Lumen 665 may have an enlarged diameter portion creating a lip 667.

During a filter retrieval process, retrieval device 600 may be advanced through a vessel to a position proximate the filter 650. Elongate shaft 620 may then be advanced distally to encounter filter 650. Ramps 642 of barbs 640 may contact bevel 668. Continued distal advancement of the elongate shaft 620 causes the appendages 635 to compress inwardly due to the sloping geometry of the bevel 668 and ramps 642. As the barbs 640 advance distal of lip 667, appendages 635 expand outwardly. The shelf 644 of barbs 640 mate with lip 667, thereby locking the filter 650 to elongate shaft 620 as shown in FIG. 11B. The interlocking geometry prevents filter 650 from disengaging with elongate shaft 620. Therefore, filter 650 may be withdrawn from a vessel by retracting the retrieval device 600 proximally.

Figure 12:
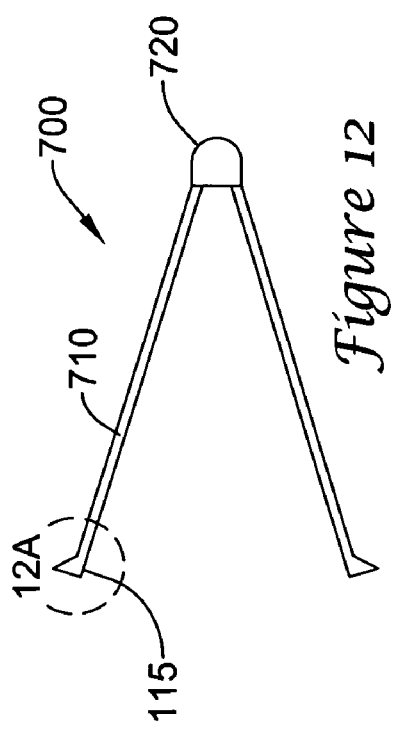
FIGS. 12-12A are plan views of a filter within the scope of the invention.
Figure 12A:
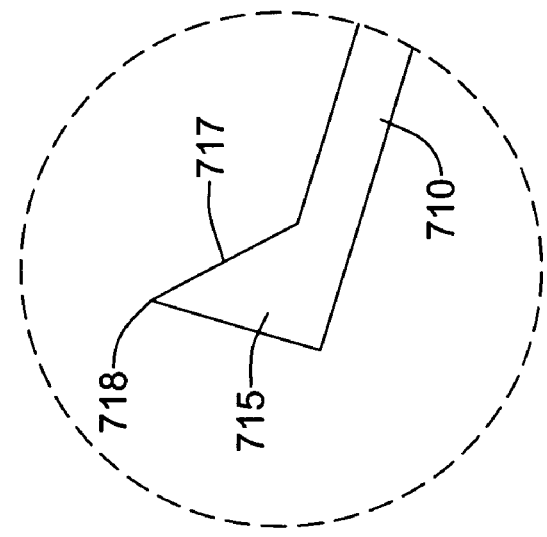

FIG. 12 illustrates a filter 700 having geometry to facilitate removal from a vessel. Filter 700 includes a plurality of legs 710 extending from a tip 720. Legs 710 have a protrusion 715 disposed at their distal end. As is more clearly shown in FIG. 12A, protrusion 715 may resemble a ramp 717 having a tapered angle and an apex 718. Protrusion 715 securely anchors filter to a vessel wall upon deployment within a vessel, while protrusion 715 subsequently may facilitate removal or repositioning filter 700. The protrusion 715 causes minimal amounts of trauma to the vessel wall due to its ramp shape. During a removal or repositioning process, an elongate sheath 730 may be advanced within the vessel to the filter 700 as shown in FIG. 13. The distal end 731 of elongate sheath 730 abuts the ramp 717 of protrusion 715. As the elongate sheath 730 is advanced distally, the distal end 731 of elongate sheath 730 urges the protrusion 715 inward to disengage the protrusion 715 from the wall 60 as shown in FIG. 13A. Because the protrusion 715 does not include a hook or barb, the legs 710 may be disengaged from the wall 60 with minimal injury to the vessel wall 60.

Figure 14:
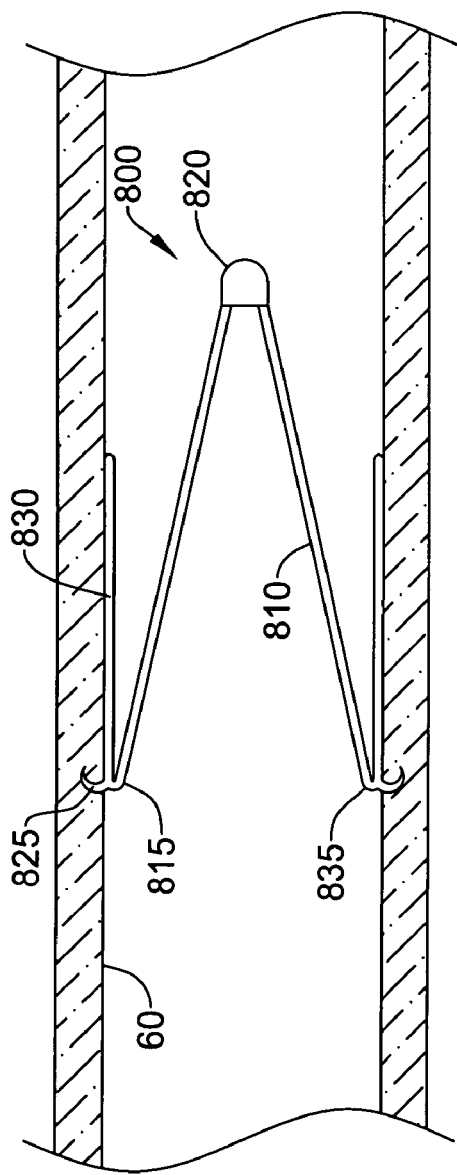
FIGS. 14-14A are cross-sectional views of a method for retrieving a filter in accordance with the invention.
Figure 14A:
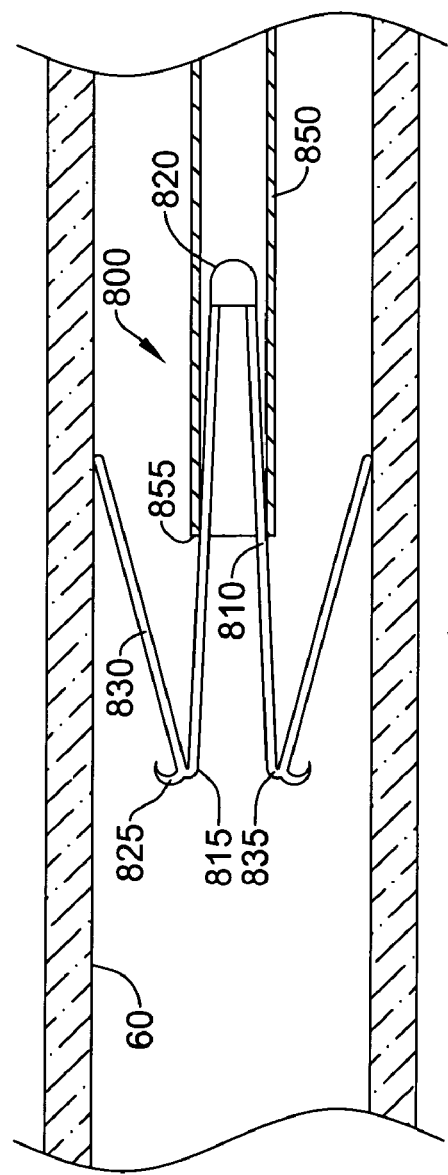

Another embodiment of a filter designed for easy removal is shown in FIG. 14A. Filter 800 includes a plurality of legs 810 extending distally from tip 820. Legs 810 include a longitudinal base portion 830 extending from the distal end 815 of legs 810. Longitudinal base portion 830 may extend either proximal or distal of distal end 815 of legs 810 or may extend in both the proximal and distal directions. Longitudinal base portion 830 helps center filter 800 within vessel wall 60, and also helps urge distal end 815 of legs 810 away from vessel wall 60 during a retrieval process. Securing hooks 825 may be attached to legs 810 at apex 835 where legs 810 adjoin longitudinal base portion 830. Securing hooks 825 may help anchor filter 800 to vessel wall 60 after deployment of filter 800.

FIG. 14B shows how longitudinal base portion 830 facilitates removal of filter 800 from a vessel. An elongate shaft 850 may be extended distally to filter 800. The distal end 855 of elongate shaft 850 may be positioned over filter tip 820 and then moved distally. Distal end 855 engages legs 810, forcing legs 810 inward. Meanwhile, longitudinal base portion 830 acts as a lever pivoting at fulcrum point 860 to facilitate disengagement of hooks 825 from vessel wall 60. The dual action of longitudinal base portion 830 and inward movement of legs 810 disengages hooks 825 from the vessel wall 60. Filter 800 may then be safely removed from or repositioned in the vessel.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What we claim is:

1. An intravascular filter placement system comprising:
   a filter having a tip and a plurality of legs extending radially outward from the tip, and
   a filter manipulation device including an outer elongate member having a proximal end, a distal end and a lumen extending therethrough and an inner elongate member disposed in at least a portion of the lumen having a proximal end and a distal end,
   wherein the inner elongate member includes a first expandable generally tubular hollow grasping member for grasping the filter during a filter manipulation process, and a second expandable generally tubular hollow grasping member for grasping the tip during a filter manipulation process, each of the first and second expandable members being disposed about the distal end of the inner elongate member, generally concentric therewith, and extending distally therefrom.

2. The intravascular filter placement system of claim 1, wherein the first expandable member is biased in an expanded position.

3. The intravascular filter placement system of claim 2, wherein the first expandable member is a braided member.

4. The intravascular filter placement system of claim 3, wherein the braided member is conical shaped.

5. The intravascular filter placement system of claim 1, wherein the first or second expandable member is an enlarged diameter portion of the inner elongate member.

6. The intravascular filter placement system of claim 1, wherein the outer elongate member includes a means for centering the outer elongate member in a vessel.

7. The intravascular filter placement system of claim 6 wherein the means for centering the outer elongate member is an inflatable balloon.

8. The intravascular filter placement system of claim 7, wherein the inflatable balloon includes a plurality of lobes.

9. The intravascular filter placement system of claim 6, wherein the means for centering the outer elongate member includes a plurality of wires including a shape memory alloy.

10. The filter manipulation device of claim 3, wherein the inner elongate member is a core wire.

11. The filter manipulation device of claim 10, further comprising a sleeve disposed at the distal end of the core wire, the sleeve securing the braided member to the core wire.

12. The filter manipulation device of claim 11, wherein the sleeve is a hypotube.

13. The filter manipulation device of claim 10, further comprising a means for centering the elongate shaft within a vessel.

14. The filter manipulation device of claim 13, wherein the means for centering the elongate shaft is an inflatable member.

15. The filter manipulation device of claim 14, wherein the inflatable member has a plurality of lobes.

16. The filter manipulation device of claim 13, wherein the means for centering the elongate shaft is a plurality of wires.

17. The filter manipulation device of claim 16, wherein the plurality of wires include a shape memory alloy.

18. The intravascular filter placement system of claim 1, wherein the second expandable member is biased in an expanded position.

19. The intravascular filter placement system of claim 18, wherein the second expandable member is a braided member.

20. The intravascular filter placement system of claim 3, wherein the second expandable member is a braided member.

21. The filter manipulation device of claim 20, wherein the second braided member is disposed within a portion of the first braided member and secured to the inner elongate member by a hypotube.

22. The filter manipulation device of claim 1, wherein the second expandable member is disposed within a portion of the first expandable member and secured to the inner elongate member.

* * * * *